(12) United States Patent
Dewey et al.

(10) Patent No.: US 12,114,901 B2
(45) Date of Patent: Oct. 15, 2024

(54) SURGICAL INSTRUMENT AND METHOD

(71) Applicant: Warsaw Orthopedic, Inc., Warsaw, IN (US)

(72) Inventors: Jonathan M. Dewey, Memphis, TN (US); Cathlene Marie Patel, Charlotte, NC (US); Fuad Nedal Mefleh, Thornton, CO (US); Abel C. Kim, Cordova, TN (US); Madelyn Dana Golding, Memphis, TN (US); Bradley Allan Melancon, Memphis, TN (US); Julien J. Prevost, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 528 days.

(21) Appl. No.: 17/246,975

(22) Filed: May 3, 2021

(65) Prior Publication Data
US 2022/0346844 A1 Nov. 3, 2022

(51) Int. Cl.
*A61B 17/70* (2006.01)
*A61B 90/00* (2016.01)

(52) U.S. Cl.
CPC .......... *A61B 17/7074* (2013.01); *A61B 90/37* (2016.02); *A61B 90/39* (2016.02); *A61B 2090/363* (2016.02); *A61B 2090/3762* (2016.02); *A61B 2090/3916* (2016.02); *A61B 2090/3937* (2016.02); *A61B 2090/3966* (2016.02); *A61B 2090/3983* (2016.02)

(58) Field of Classification Search
CPC ........................................ A61B 17/7074–7092
See application file for complete search history.

(56) References Cited

U.S. PATENT DOCUMENTS

| | | | | |
|---|---|---|---|---|
| 6,226,548 | B1* | 5/2001 | Foley | A61B 17/70 600/426 |
| 7,547,307 | B2* | 6/2009 | Carson | A61B 17/154 606/88 |
| 8,233,963 | B2* | 7/2012 | Hartmann | A61B 90/36 600/424 |
| 8,644,907 | B2* | 2/2014 | Hartmann | A61B 34/20 600/424 |
| 8,939,995 | B2* | 1/2015 | Lechner | A61L 31/126 606/217 |
| 9,179,984 | B2* | 11/2015 | Teichman | A61B 34/20 |
| 9,220,573 | B2* | 12/2015 | Kendrick | A61B 90/39 |
| 9,848,922 | B2* | 12/2017 | Tohmeh | A61B 17/7086 |

(Continued)

*Primary Examiner* — Eduardo C Robert
*Assistant Examiner* — Steven J Cotroneo
(74) *Attorney, Agent, or Firm* — Sorell, Lenna & Schmidt, LLP

(57) ABSTRACT

A surgical system includes a first surgical instrument having a selected configuration and an image guide disposed relative to a sensor to communicate a signal representative of a position of the image guide. A passive image guide is fixed with vertebral tissue and is disposed relative to the sensor to communicate a signal representative of a position of the passive image guide. The passive image guide includes a first surface. A second surgical instrument is connectable with the first surgical instrument and includes a second surface engageable with the first surface in a mating configuration to provide verification of the selected configuration. Surgical instruments, implants, spinal constructs and methods are disclosed.

20 Claims, 16 Drawing Sheets

(56) References Cited

U.S. PATENT DOCUMENTS

| | | | | |
|---|---|---|---|---|
| 10,004,609 | B2* | 6/2018 | Palmatier | A61F 2/4611 |
| 10,285,715 | B2* | 5/2019 | Peters | A61B 17/1655 |
| 11,389,252 | B2* | 7/2022 | Gera | A61B 90/36 |
| 11,660,144 | B2* | 5/2023 | Garcia | A61B 34/10 |
| | | | | 606/130 |
| 2006/0264742 | A1* | 11/2006 | Neubauer | A61B 90/98 |
| | | | | 600/424 |
| 2007/0016009 | A1* | 1/2007 | Lakin | A61B 90/39 |
| | | | | 600/424 |
| 2015/0105833 | A1 | 4/2015 | Simpson et al. | |
| 2017/0354426 | A1* | 12/2017 | Glard | A61B 90/10 |
| 2018/0296283 | A1* | 10/2018 | Crawford | G06T 3/02 |
| 2020/0330160 | A1* | 10/2020 | Dace | A61B 17/1671 |
| 2021/0361357 | A1* | 11/2021 | Crawford | A61B 34/20 |
| 2022/0346895 | A1* | 11/2022 | Crawford | A61B 17/1659 |

* cited by examiner

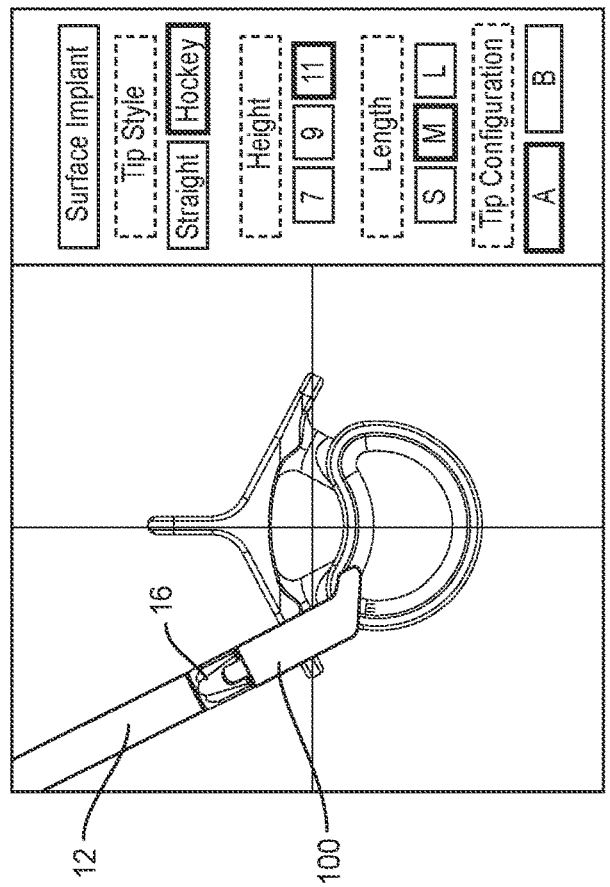
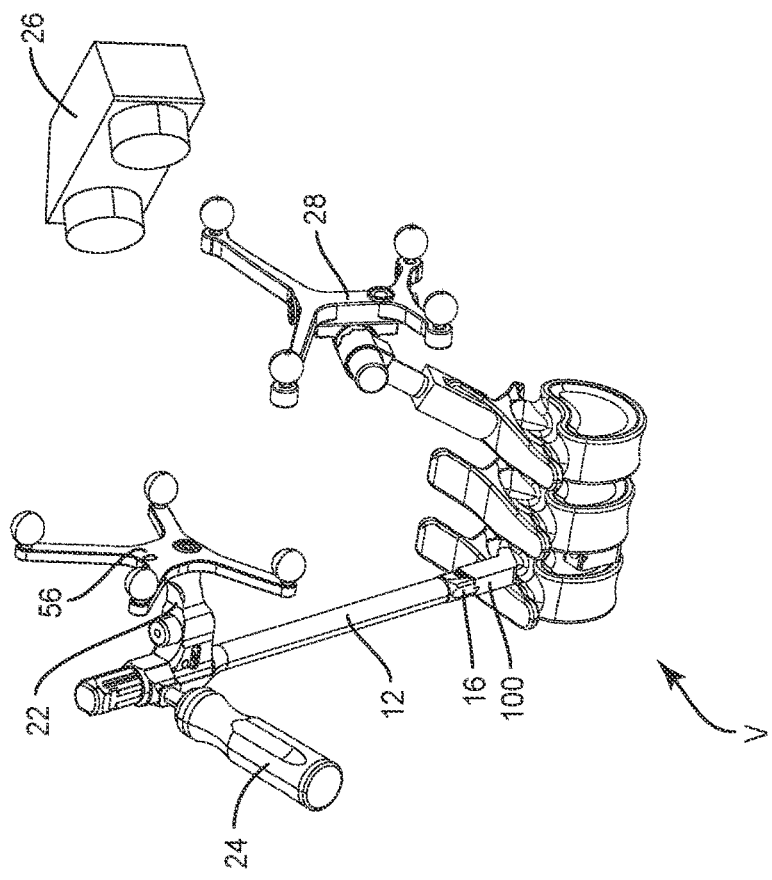
FIG. 16
FIG. 15

SURGICAL INSTRUMENT AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical system is provided. The surgical system includes a first surgical instrument having a selected configuration and an image guide disposed relative to a sensor to communicate a signal representative of a position of the image guide. A passive image guide is fixed with vertebral tissue and is disposed relative to the sensor to communicate a signal representative of a position of the passive image guide. The passive image guide includes a first surface. A second surgical instrument is connectable with the first surgical instrument and includes a second surface engageable with the first surface in a mating configuration to provide verification of the selected configuration. In some embodiments, surgical instruments, implants, spinal constructs and methods are provided.

In one embodiment, a surgical instrument is provided. The surgical instrument includes a body having a first surface and is connectable with a surgical inserter. The surgical inserter has a selected configuration and an image guide is disposed relative to a sensor to communicate a signal representative of a position of the image guide. The first surface is engageable with a second surface of a passive image guide fixed with vertebral tissue and is disposed relative to the sensor to communicate a signal representative of a position of the passive image guide. The first surface is engageable with the second surface in a mating configuration to provide verification of the selected configuration.

In one embodiment, a method for treating a spine is provided. The method comprises the steps of: selecting a first surgical instrument having a selected configuration and an image guide disposed relative to a sensor, the sensor communicating a signal representative of a position of the image guide; connecting a second surgical instrument with the first surgical instrument; engaging a first surface of the first surgical instrument with a second surface of a passive image guide fixed with vertebral tissue and disposed relative to the sensor to communicate a signal representative of a position of the passive image guide, the first surface being engageable with the second surface in a mating configuration to provide verification of the selected configuration.

BRIEF DESCRIPTION OF THE DRAWINGS

The present disclosure will become more readily apparent from the specific description accompanied by the following drawings, in which:

FIG. 15 is a perspective view of components of one embodiment of a surgical system in accordance with the principles of the present disclosure disposed with vertebrae;

FIG. 16 is a graphical representation of a computer display of components of one embodiment of a surgical system in accordance with the principles of the present disclosure;

DETAILED DESCRIPTION

Figure 1:
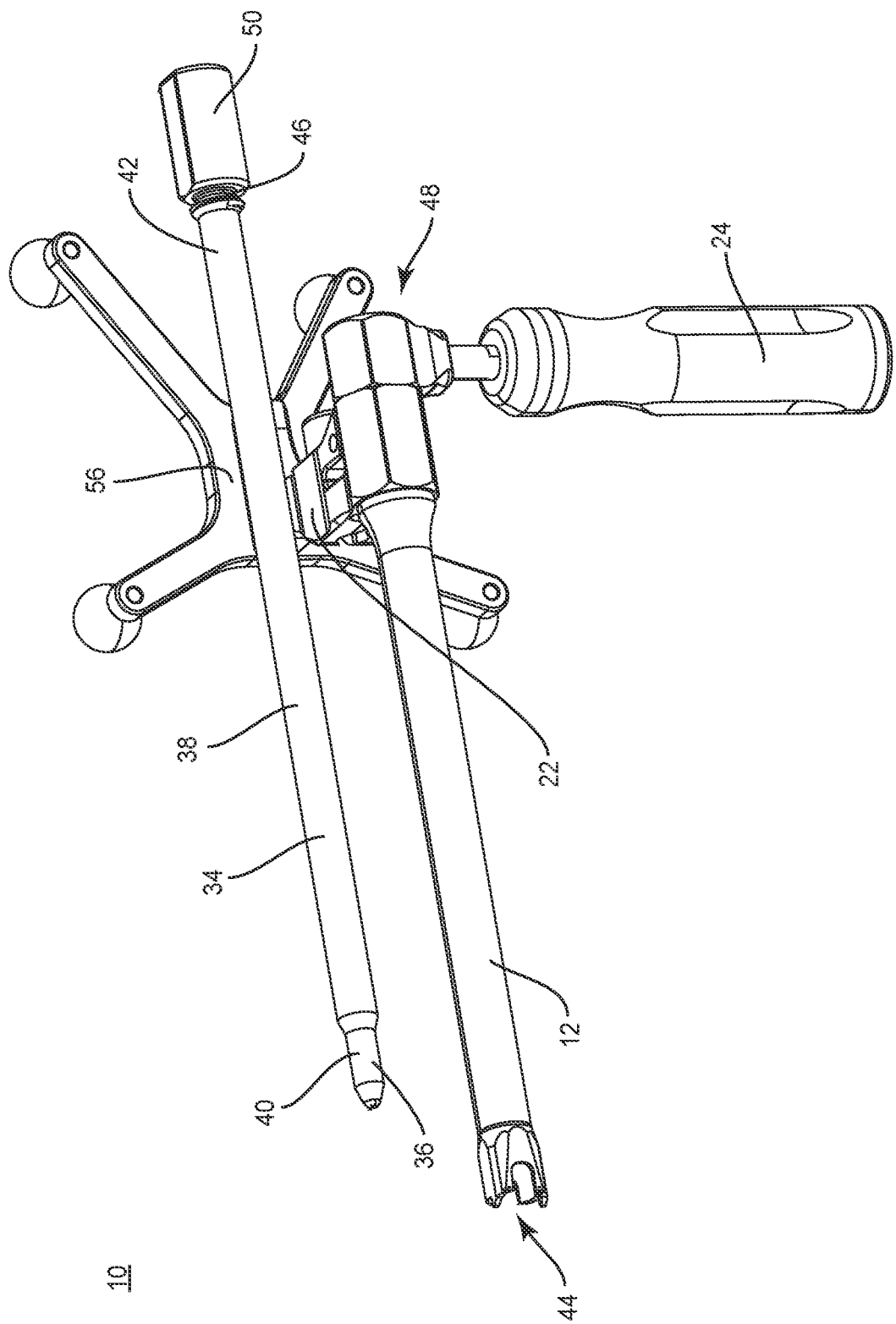
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the systems and methods of the present disclosure comprise surgical navigation and medical devices including surgical instruments and implants that are employed with a surgical treatment, as described herein, for example, with a cervical, thoracic, lumbar and/or sacral region of a spine. The present surgical system includes a surgical instrument, for example, a surgical inserter having a selected configuration and being connectable with a surgical verification instrument to verify the selected configuration of the surgical inserter in connection with a surgical treatment.

In some embodiments, the present surgical system includes a passive image guide, for example, attached with a patient during a surgical procedure and engageable with a surgical inserter having a selected configuration, which includes an image guide of the surgical inserter being disposable a selected distance from the passive image guide. In some embodiments, one or more components of the present surgical system are disposable relative to a sensor to communicate a signal representative of a position of one or more components of the present surgical system, for example, a distance of the image guide of the surgical inserter relative to the passive image guide. In some embodiments, a surgical verification instrument is connected with the surgical inserter and engageable with the passive image guide to verify the selected configuration. In some embodiments, a surface of the surgical verification instrument is engaged with a surface of the passive image guide in a mating configuration to provide verification of a selected configuration of the surgical inserter.

In some embodiments, the present surgical system includes one or more surgical instruments including a surgical verification instrument, a surgical inserter, an image guide and a passive image guide. In some embodiments, the surgical verification instrument includes a stylet that is inserted into the surgical inserter. In some embodiments, the surgical verification instrument is inserted through a hollow channel of the surgical inserter. In some embodiments, the surgical verification instrument is configured for threaded connection with the surgical inserter. In some embodiments, the surgical verification instrument is inserted into the surgical inserter to provide verification of a selected configuration of the surgical inserter. In some embodiments, the surgical verification instrument provides verification for a spinal implant, a trial or an instrument for a surgical procedure before they are implemented by a user in the surgical procedure. In some embodiments, connection between the surgical inserter and the surgical verification instrument enables a user to determine whether a main shaft of the surgical inserter is deformed.

In some embodiments, the present surgical system includes one or more surgical instruments, including a surgical verification instrument that is insertable into a channel of a surgical inserter to verify the selected configuration of the surgical inserter for a selected implant in connection with a surgical treatment. In some embodiments, the surgical verification instrument is configured for connection with the surgical inserter and a passive image guide. In some embodiments, the surgical inserter includes an image guide. In some embodiments, an end of the surgical verification instrument includes a surface that is configured for engagement with a surface of the passive image guide. In some embodiments, the one or more surgical instruments are implemented with a surgical navigation system to verify instruments in a surgical procedure. In some embodiments, the surgical navigation system includes one or more cameras that spatially recognize the location and/or distance of components of the image guide and the passive image guide relative to each other. In some embodiments, the surgical navigation system includes software that compares data, for example, data relating to a distance between components of the image guide and the passive image guide acquired by the one or more cameras, and compares the data to data stored in the software for a selected surgical inserter. In some embodiments, the stored data includes data relating to a distance between components of an image guide that is paired with a selected surgical inserter and a passive image guide. In some embodiments, the data is compared to verify the selected configuration of the surgical inserter in connection with a surgical treatment. In some embodiments, the distance between the image guide and the passive image guide is determined by the mating engagement between the surgical verification instrument and the passive image guide.

In some embodiments, the present surgical system includes one or more surgical instruments and is employed with a method including the step of selecting a surgical verification instrument and a surgical inserter. In some embodiments, the present surgical system is employed with methods including the step of inserting the surgical verification instrument into the surgical inserter. In some embodiments, the surgical verification instrument is inserted into a channel of the surgical inserter. In some embodiments, a threaded end of the surgical verification instrument engages a threaded inner surface of the surgical inserter to lock the surgical verification instrument with the surgical inserter.

In some embodiments, the present surgical system is employed with methods including the step of selecting a software program for use with a processor of the surgical system. In some embodiments, the present surgical system is employed with methods including the step of adding the surgical inserter into a procedure menu of the software program that is displayed on a computer monitor via a graphical user interface. In some embodiments, the surgical inserter is preloaded into the software program, see for example, those programs associated with Stealth Station™ software owned by Medtronic Inc., Minnesota, U.S.A. In some embodiments, patient data is added to the software program manually or via a data storage device, for example, a flash drive. In some embodiments, a software package, for example, a tool card is loaded with instruments and spinal implants for implementation in the surgical procedure and is loaded into the software program. In some embodiments, the tool card is preloaded in the procedure and the surgical inserter can be selected from available tools loaded in the software program. In some embodiments, the surgical inserter is added into the tools in procedure menu. In some embodiments, during use of the software program, a new surgical instrument can be added to a tools in procedure menu that is displayed on the computer monitor via a graphical user interface. In some embodiments, a new instrument can be added into the procedure via a button that prompts a user to click to add a new instrument. In some embodiments, a drop down menu is provided.

In some embodiments, the present surgical system is employed with methods including the step of selecting a surgical inserter tip configuration. In some embodiments, a drop down menu is displayed on the computer monitor via a graphical user interface to select the tip configuration. In some embodiments, a border is disposed about the surgical inserter selection and is displayed on the computer monitor via a graphical user interface to visually confirm the surgical inserter selection. In some embodiments, a bar is displayed on the computer monitor via a graphical user interface to visually confirm surgical inserter selection. In some embodiments, the bar is visual indicia of a warning to a user as to whether the surgical inserter has been verified. In some embodiments, the bar includes diagonal hash lines, colored lines, and/or wording to indicate that the surgical inserter has or has not been verified. In some embodiments, the bar is displayed at all times on the computer monitor. In some embodiments, an image guide, including an image guide orientation is selected and added to the tools in procedure menu.

In some embodiments, the present surgical system is employed with methods including the step of positioning the surgical verification instrument connected to the surgical inserter above the passive image guide. In some embodiments, the present surgical system is employed with methods including the step of inserting a mating surface tip of the surgical verification instrument into a mating surface, for example, a divot of the passive image guide. In some embodiments, the present surgical system is employed with methods including the step of confirming the selected surgical inserter with the software described above. In some embodiments, after the surgical verification instrument has been properly mated with the passive image guide, the software and/or the hardware is configured to verify that the image guide disposed on the surgical inserter is the proper distance from the passive image guide to verify that the selected surgical inserter is ready for use in a surgical procedure. In some embodiments, the surgical inserter will not be verified by the software program if the surgical verification instrument and the passive image guide are improperly mated. In some embodiments, the surgical verification instrument and the passive image guide are improperly mated when the distance between the image guide and the passive image guide is different than the distance stored as data in the software program.

In some embodiments, the surgical verification instrument is selected in the tools in procedure menu as described above of the software program as described above, and the image in the procedure reflects the selected surgical verification instrument. In some embodiments, a drop down box is provided and is displayed on the computer monitor via a graphical user interface. In some embodiments, the computer monitor alternates between a surgical verification instrument menu and an implant menu. In some embodiments, a drop down box is displayed on the computer monitor to alternate between the surgical verification instrument and the implant menu. In some embodiments, when an implant option is selected in the tools in procedure menu, images and options in the procedure indicate the implant. In some embodiments, the options are slider menus and/or drop down menus.

In some embodiments, the present surgical system includes a surgical instrument including a surgical verification instrument that is connectable with a surgical inserter and a passive image guide. In some embodiments, the surgical verification instrument includes a body and a cap. In some embodiments, the cap includes a threaded inner surface that is connectable with a threaded end of the body. In some embodiments, the body includes an inner sleeve. In some embodiments, the cap includes a verification tip. In some embodiments, the tip is pointed. In some embodiments, the body of the surgical verification instrument is inserted into the surgical inserter and the cap is threaded with the threaded end of the body. In some embodiments, the surface of the tip engages with a surface of the passive image guide in a mating engagement. In some embodiments, the tip is configured for engagement with an implant to retain the implant with the surgical inserter. In some embodiments, the tip is cone shaped and the surface of the passive image guide is a cone shaped recess. In some embodiments, the tip is ball shaped and the surface of the passive image guide is a socket shaped recess.

In some embodiments, the present surgical system includes a surgical instrument, for example, an implant surgical inserter employed with a method of using a navigation system in navigated spine procedures. In some embodiments, the surgical instrument can be employed with optical-based navigation systems to facilitate surgical instrument line of sight between an instrument image guide and a camera. In some embodiments, this configuration facilitates the ability to consistently track surgical instrument position throughout a surgical procedure in connection with location of a navigation camera in an operating room and for patient positioning.

In some embodiments, the present surgical system includes a surgical instrument that has an image guide, for example, a tracker. In some embodiments, the tracker provides indicia and/or display of a location and angulation of the surgical instrument. In some embodiments, the surgical system includes a surgical instrument having one or more image guides, which include one or more fiducial markers. In some embodiments, the fiducial marker includes a single ball-shaped marker. In some embodiments, the image guide is disposed adjacent a proximal end of the surgical instrument. In some embodiments, the image guide provides indicia and/or display of a precise rotational and/or linear position of the image guide on the surgical instrument. In some embodiments, this configuration provides indicia and/or display of an amount of manipulation, movement, translation and/or rotation of the implant with tissue.

In some embodiments, the surgical system includes an O-arm medical imaging device that digitally captures images of an anatomy. In some embodiments, the tracker communicates with a surgical navigation system to determine and/or display surgical instrument positioning relative to the anatomy.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease.

For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system including surgical navigation, surgical instruments, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-17, there are illustrated components of a surgical system 10.

The components of surgical system 10 can be fabricated from biologically acceptable materials suitable for medical applications, including metals, synthetic polymers and/or ceramics. For example, the components of surgical system 10, individually or collectively, can be fabricated from materials such as stainless steel alloys, aluminum, commercially pure titanium, titanium alloys, Grade 5 titanium, superelastic titanium alloys, cobalt-chrome alloys, superelastic metallic alloys (e.g., Nitinol, super elasto-plastic metals, such as GUM METAL®), ceramics, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene and/or epoxy.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a fully open surgical procedure, a minimally invasive procedure including percutaneous techniques, and mini-open surgical techniques to deliver and introduce instrumentation and/or one or more implants at a surgical site within a body of a patient, for example, a section of a spine. In some embodiments, one or more surgical instruments of surgical system 10 can be configured to deliver and introduce one or more components of a spinal construct, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Surgical system 10 includes a surgical instrument, for example, a surgical inserter 12 having a selected configuration, as shown in FIG. 1. In some embodiments, the selected configuration includes an engagement portion 20 being disposed at a selected distance from an image guide 22. In some embodiments, the selected configuration corresponds to the configuration of engagement portion 20 for connection with a particular spinal implant, for example, a spinal implant 100, use and/or surgical treatment. In some embodiments, the selected configuration can include a length, diameter and/or cross section configuration of surgical inserter 12.

In some embodiments, surgical inserter 12 is selected from a plurality of surgical inserters 12. In some embodiments, each surgical inserter 12 includes a different selected configuration. In some embodiments, the plurality of surgical inserters 12 includes a surgical inserter 12 having a first selected configuration and a surgical inserter 12 having a second selected configuration. In some embodiments, engagement portion 20 of the first selected configuration is different than engagement portion 20 of the second selected configuration. In some embodiments, engagement portion 20 is configured for mating with a portion of a selected corresponding implant 100. In some embodiments, implant 100 is variously configured including a straight or angled implant 100. In some embodiments, implant 100 includes a selected length and/or height.

Figure 2:
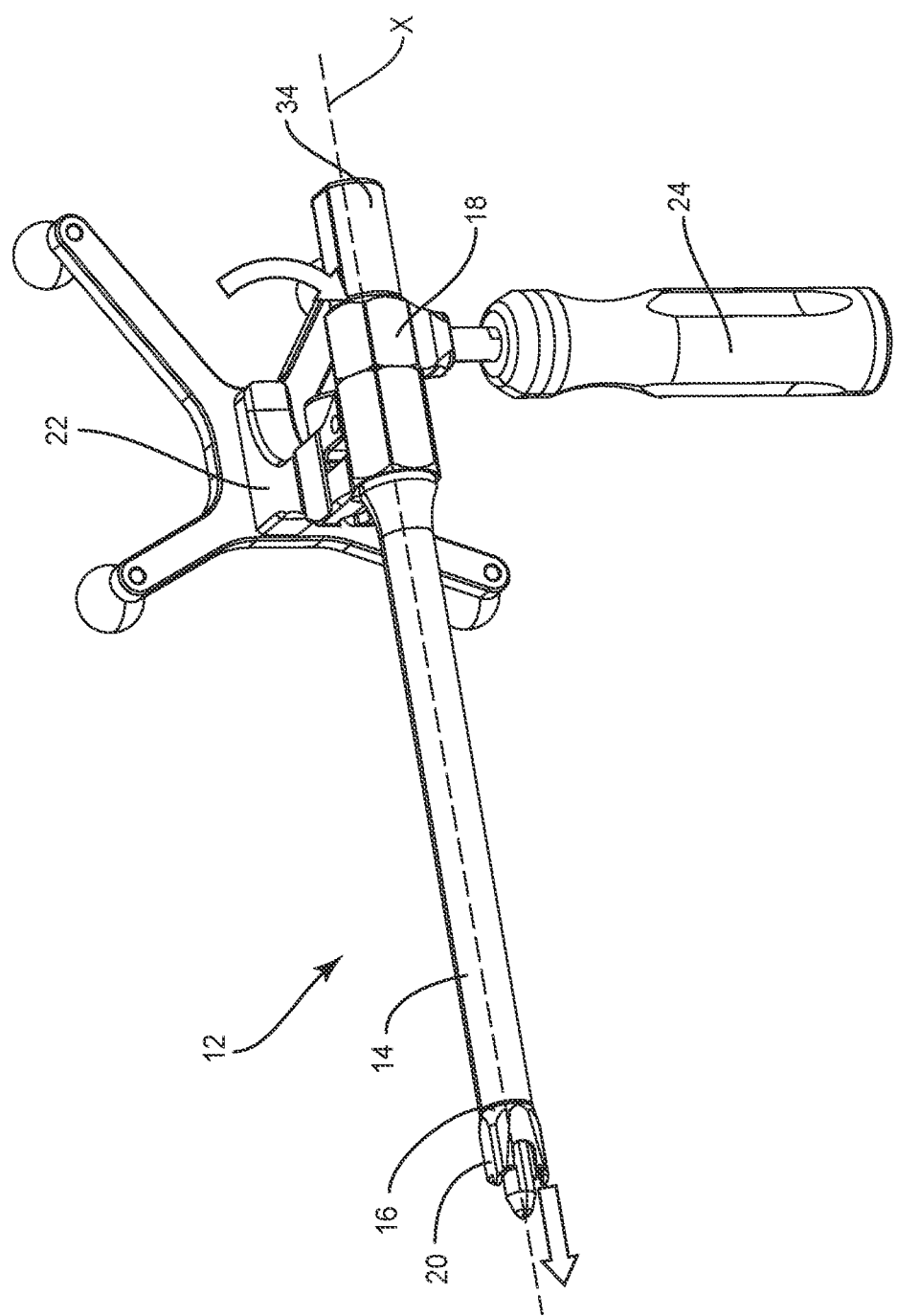
FIG. 2 is a perspective view of the components shown in FIG. 1.
Figure 3:
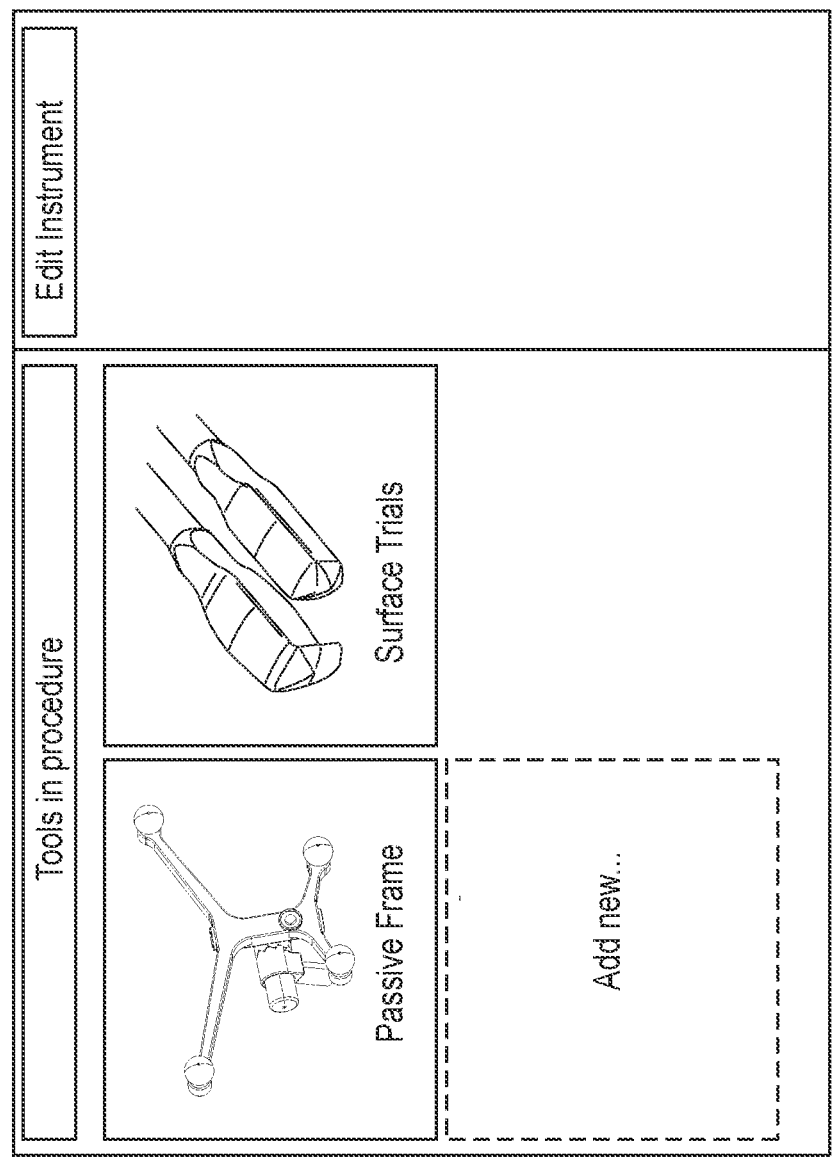
FIG. 3 is a graphical representation of a computer display of components of one embodiment of a surgical system in accordance with the principles of the present disclosure.
Figure 4:
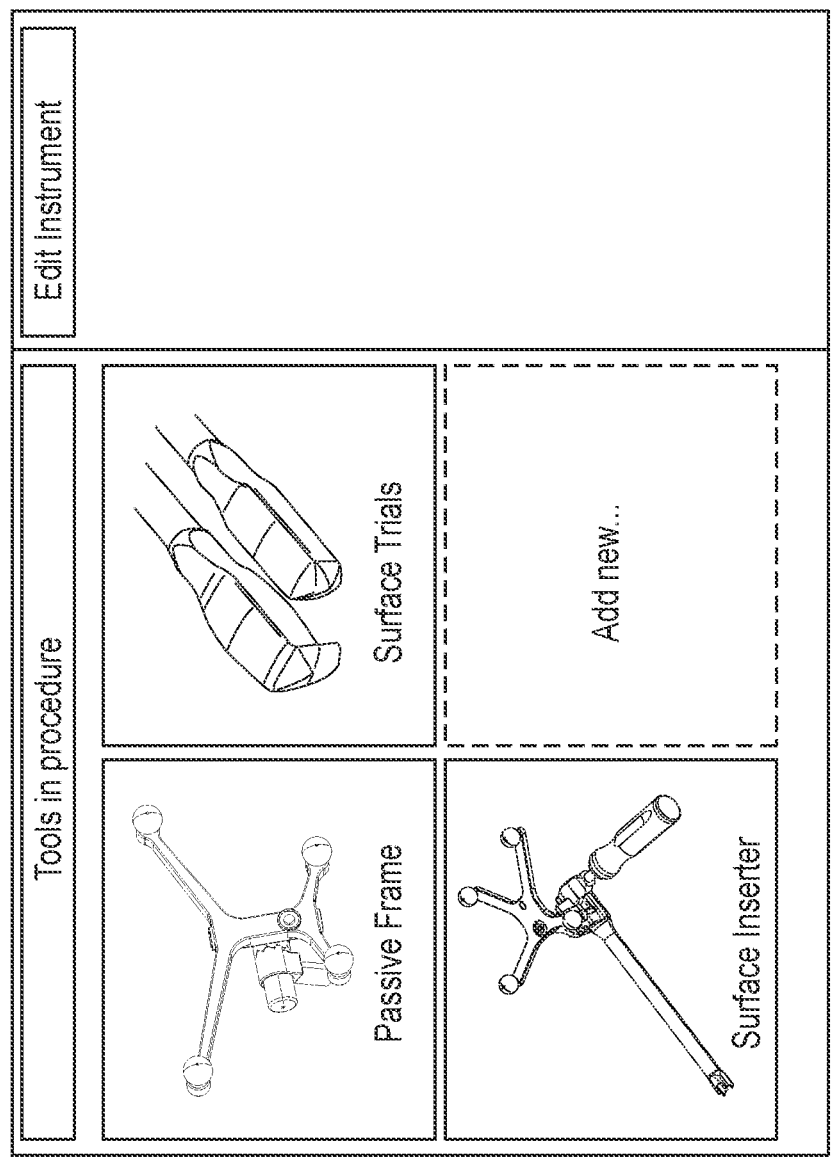
FIG. 4 is a graphical representation of a computer display of components of one embodiment of a surgical system in accordance with the principles of the present disclosure.
Figure 7:
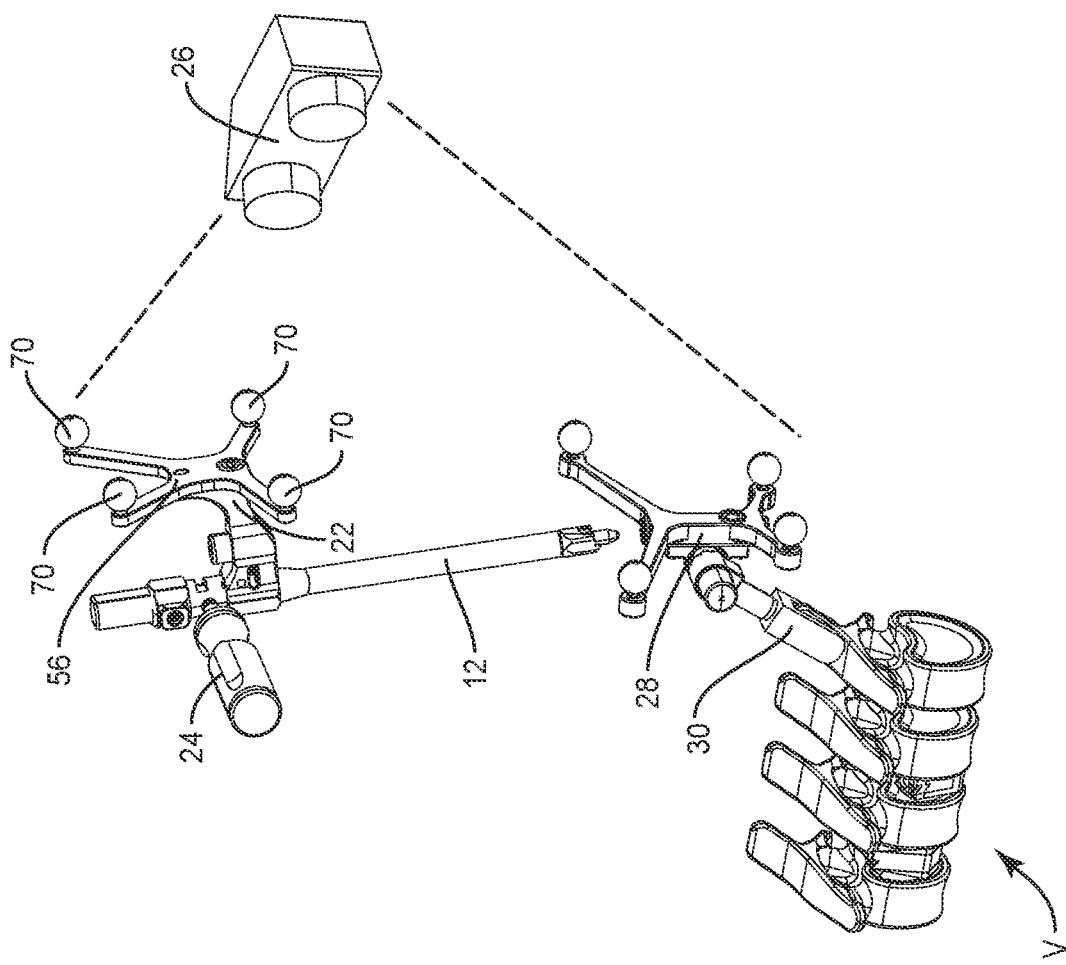
FIG. 7 is a perspective view of components of one embodiment of a surgical system in accordance with the principles of the present disclosure disposed with vertebrae.

Surgical inserter 12 is configured for connection with a surgical instrument, for example, a surgical verification instrument 34, as shown in FIG. 2, to verify the selected configuration of surgical inserter 12 in connection with a selected implant 100, a surgical treatment and/or a surgical procedure. Surgical inserter 12 includes a shaft 14 that extends between an end 16, an end 18 and defines a longitudinal axis X, as shown in FIG. 2. End 16 includes engagement portion 20, as described herein and shown in FIGS. 15 and 16. End 18 is connected with a navigation component, for example, image guide 22 and a handle 24, as described herein. Image guide 22 is disposed relative to a sensor, for example, a sensor array 26 to communicate a signal representative of a position of image guide 22, as shown in FIG. 7. Image guide 22 is disposed relative sensor 26 for alignment and detection of a signal with sensor array 26 of a navigation system 200. Image guide 22 is attached with end 18 at a selected distance from one or more components of surgical inserter 12 when connected with surgical inserter 12 to represent position and/or orientation of image guide 22, as described herein.

In some embodiments, handle 24 may be disposed at alternate orientations relative to shaft 14, for example, parallel, perpendicular and/or other angular orientations such as acute or obtuse, co-axial, offset, and/or staggered. In some embodiments, handle 24 may include alternate surface configurations to enhance gripping of handle 24, for example, rough, arcuate, undulating, mesh, porous, semi-porous, dimpled and/or textured. In some embodiments, handle 24 may include alternate cross section configurations, for example, oval, oblong, triangular, square, hexagonal, polygonal, irregular, uniform, non-uniform and/or tapered.

A passive image guide 28 is fixed with tissue, for example, vertebral tissue and is disposed relative to sensor array 26 to communicate a signal representative of a position of passive image guide 28, as shown in FIG. 7. In some embodiments, passive image guide 28 is fixed to patient anatomy in a region of a body which is to receive implant 100. Passive image guide 28 includes a frame 30 fixed with the vertebral tissue, as described herein and shown FIG. 7. In some embodiments, by sensing passive image guide 28, sensor array 26 can determine the position of patient anatomy in a detector space.

Figure 8:
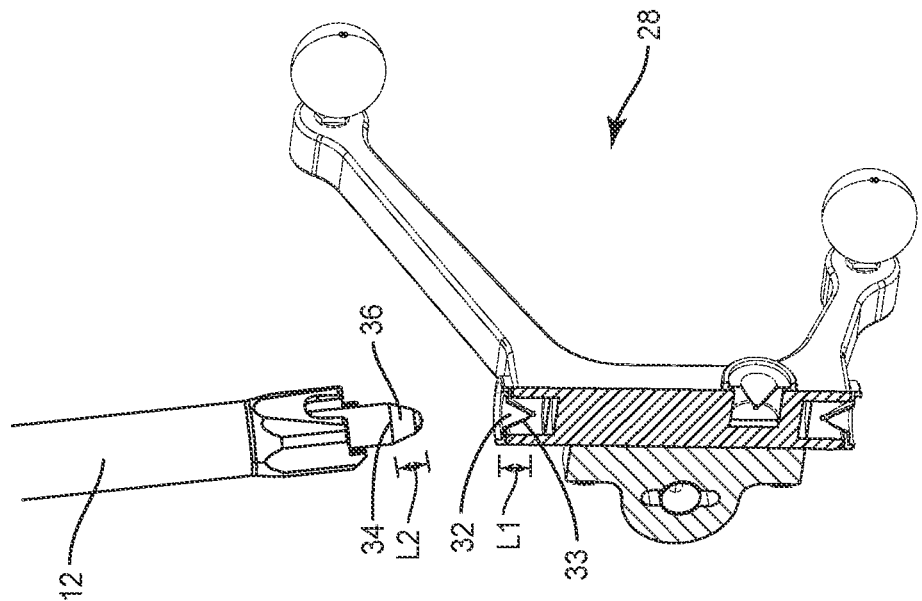
FIG. 8 is a break away view partially in cross section of components of the surgical system shown in FIG. 7.

Passive image guide 28 includes a surface 32, as shown in FIG. 8. Surface 32 is configured for engagement with a surface 36 of surgical verification instrument 34 in a mating configuration to provide verification of the selected configuration, as described herein. Surface 32 includes a recess 33, as shown in FIG. 8. Recess 33 includes a length L1, as shown in FIG. 8 and described herein. In some embodiments, length L1 is in a range from 1 to about 20 mm. In some embodiments, recess 33 may be variously configured including tapered, cone shaped, threaded and/or socket shaped. In some embodiments, recess 33 may include alternate cross section configurations, for example, for example, triangular, scalene triangle, right triangle, pyramidal, square, circular, oval, rectangular, pentagonal, hexagonal, heptagonal, octagonal, nonagon, parallelogram, rhombus, U-shaped, V-shaped, W-shaped, concave, crescent, heart, cross, arrow, cube, cylinder, star, a wavy line, semicircular, ring, quatrefoil, irregular, uniform, non-uniform, tapered or a combination thereof. In some embodiments, surface 32 may include alternate surface configurations, for example, rough, arcuate, undulating, mesh, porous, semi-porous, dimpled and/or textured.

Surgical verification instrument 34 includes a body 38 that extends between an end 40, an end 42 and is disposed along longitudinal axis X, as shown in FIG. 2. Surgical verification instrument 34 is configured for coaxial connection with surgical inserter 12 via disposal of surgical verification instrument 34 through a cavity 44 of surgical inserter 12. Cavity 44 is centrally disposed within surgical inserter 12. In some embodiments, surgical verification instrument 34 includes a stylet configuration. In some embodiments, surgical verification instrument 34 may include alternate surface configurations, for example, rough, arcuate, undulating, mesh, porous, semi-porous, dimpled and/or textured. In some embodiments, surgical verification instrument 34 may include alternate cross section configurations, for example, oval, oblong, triangular, square, hexagonal, polygonal, irregular, uniform, non-uniform and/or tapered.

End 40 includes surface 36. Surface 36 includes a length L2, as shown in FIG. 8. Length L2 corresponds to length L1 and is configured to be approximately equal in length to L1. In some embodiments, Length L2 is in a range from 1 to about 20 mm. In some embodiments, surface 36 may be variously configured including tapered, cone shaped, threaded and/or ball shaped. In some embodiments, surface 36 may include alternate cross section configurations, for example, triangular, scalene triangle, right triangle, pyramidal, square, circular, oval, rectangular, pentagonal, hexagonal, heptagonal, octagonal, nonagon, parallelogram, rhombus, U-shaped, V-shaped, W-shaped, concave, crescent, heart, cross, arrow, cube, cylinder, star, a wavy line, semicircular, ring, quatrefoil, irregular, uniform, non-uniform, tapered or a combination thereof. In some embodiments, surface 36 may include alternate surface configurations, for example, rough, arcuate, undulating, mesh, porous, semi-porous, dimpled and/or textured.

In some embodiments, surface 36 includes a tapered projection that is matingly engaged with a correspondingly configured recess 33 of surface 32. In some embodiments, surface 36 includes a cone shaped projection matingly engaged with a correspondingly configured cone shaped recess 33 of surface 32. In some embodiments, surface 36 is fully threaded with surface 32. In some embodiments, surface 36 includes a ball shaped projection matingly engaged with a socket shaped recess 33 of surface 32.

End 42 includes an outer surface that defines a threaded portion 46, as shown in FIG. 1. Threaded portion 46 is configured for threaded engagement with a threaded portion 48 of cavity 42 of surgical inserter 12. Threaded portion 46 engages with threaded portion 48 of cavity 44 when surgical verification instrument 34 is disposed within cavity 44 of surgical inserter 12 to connect surgical verification instrument 34 with surgical inserter 12. End 42 includes a handle 50. In some embodiments, handle 50 may be disposed at alternate orientations relative to body 38, for example, parallel, perpendicular and/or other angular orientations such as acute or obtuse, co-axial, offset, and/or staggered. In some embodiments, handle 50 may include alternate surface configurations to enhance gripping of handle 50, for example, rough, arcuate, undulating, mesh, porous, semi-porous, dimpled and/or textured. In some embodiments, handle 50 may include alternate cross section configurations, for example, oval, oblong, triangular, square, hexagonal, polygonal, irregular, uniform, non-uniform and/or tapered.

Figure 9:
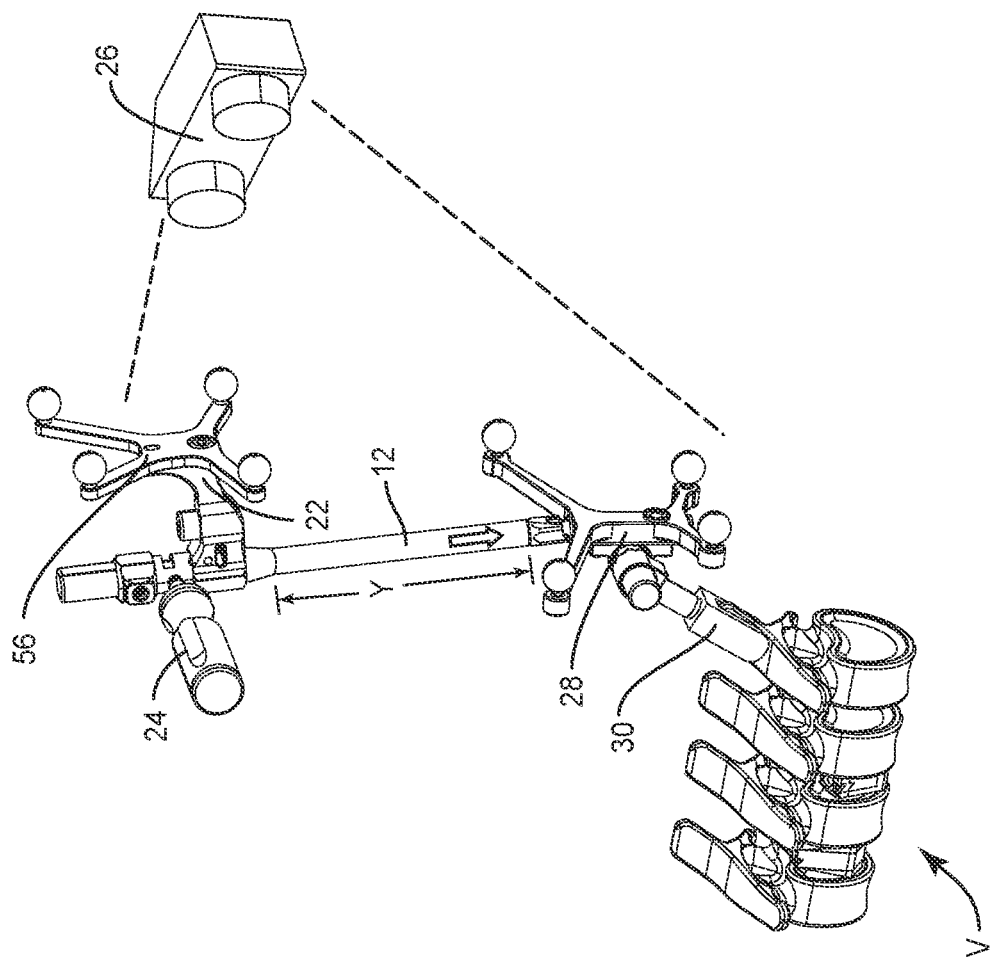
FIG. 9 is a perspective view of components of one embodiment of a surgical system in accordance with the principles of the present disclosure disposed with vertebrae.

As described herein, the engagement of surface 32 and surface 36 in a mating configuration provides verification of the selected configuration of surgical inserter 12. When surfaces 32, 36 are in the mating configuration, image guide 22 is disposed at a selected distance Y from passive image guide 28, as shown in FIG. 9. In some embodiments, in the mating configuration, image guide 22 is disposed at a selected distance from frame 30 of passive image guide 28. The selected distance Y between image guide 22 and passive image guide 28 verifies the selected configuration of surgical inserter 12 in connection with the surgical procedure. In some embodiments, distance Y is in a range of 5 through 400 mm. In some embodiments, distance Y extends a selected distance within an accuracy and/or tolerance of ±0.25 mm. In some embodiments, distance Y extends a selected distance within an accuracy and/or tolerance of ±0.12 mm.

Sensor array 26 communicates with a computer 52, including a processor, which may be programmed with software modules that analyze signals transmitted by sensor array 26 to determine the position of each object, for example, image guide 22 and passive image guide 28 in a detector space. Sensor array 26 communicates with computer 52 to verify properly mated surfaces 32, 36 and to confirm engagement by measuring distance Y between image guide 22 and passive image guide 28. In some embodiments, surfaces 32, 36 are properly mated when surfaces 32, 36 are in a flush engagement and/or in an abutted engagement. In some embodiments, computer 52 verifies mated surfaces 32, 36 by measuring distance Y and overlapping lengths L1 and L2. Surgical inserter 12 will not be verified by the software/computer 52 when surfaces 32, 36 are improperly mated. In some embodiments, improperly mated surfaces 32, 36 include a distance Y that is different than a distance Y that is stored as data in computer 52/software program.

Figure 17:
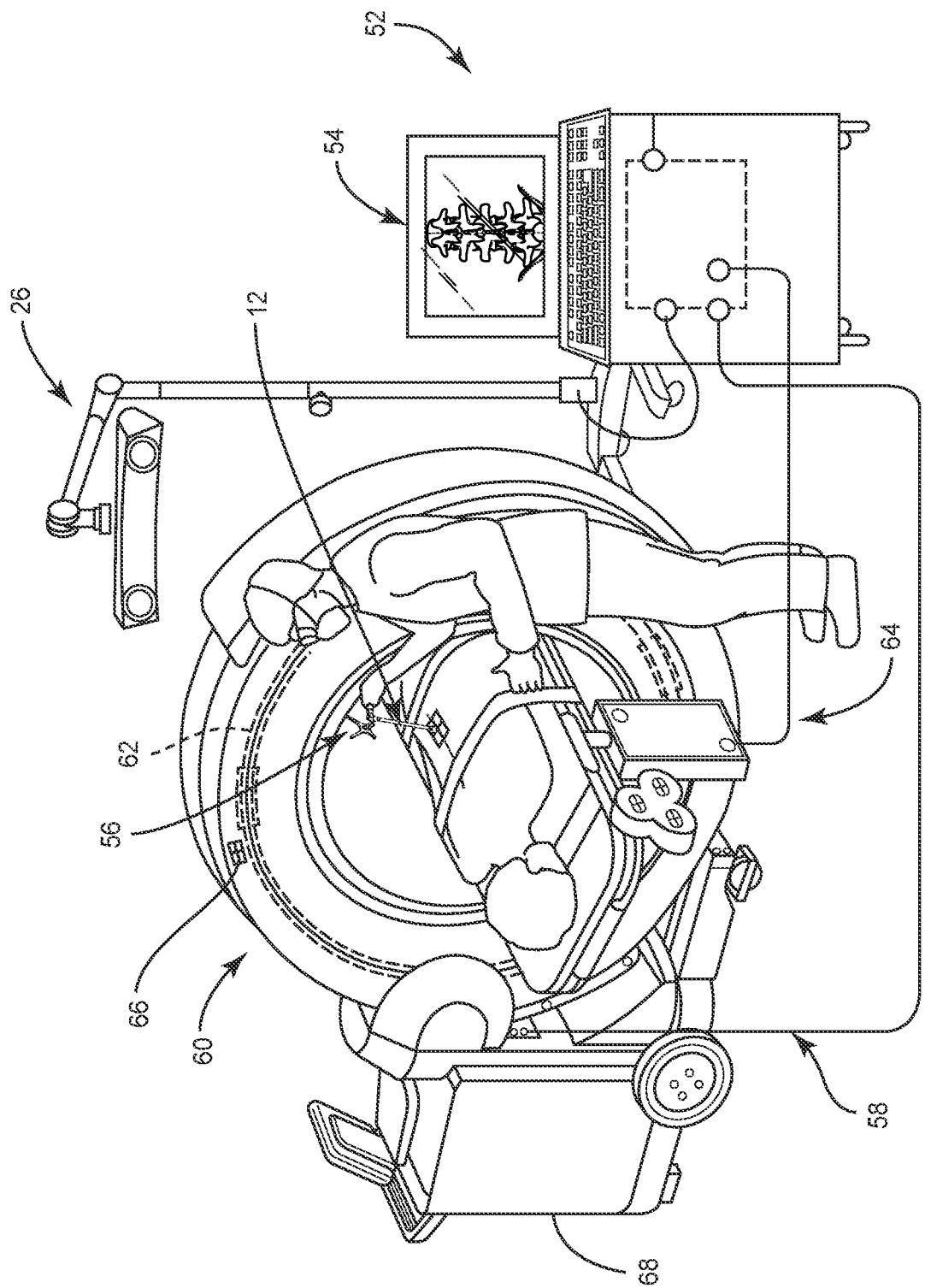
FIG. 17 is a perspective view of components of one embodiment of a surgical system in accordance with the principles of the present disclosure.

In some embodiments, computer 52 provides selected configuration verification indicia, including audible, tactile or visual indicia. In some embodiments, the processor of computer 52 communicates with a computer monitor 54 to provide visual indicia verification of the selected configuration via monitor 54, as shown in FIG. 17 and described herein.

Image guide 22 includes an emitter array 56. Emitter array 56 is configured for generating a signal to sensor array 26 of a surgical navigation system 58, as shown in FIG. 17 and described herein. The signal generated by emitter array 56 represents a position of image guide 22 relative to passive image guide 28. In some embodiments, the signal generated by emitter array 56 represents a position of implant 100 relative to surgical inserter 12 and relative to tissue, for example, bone. In some embodiments, the signal generated by emitter array 56 represents a three dimensional position of implant 100 relative to tissue.

In some embodiments, image guide 22 may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

In some embodiments, sensor array 26 receives signals from emitter array 56 to provide a three-dimensional spatial position and/or a trajectory of image guide 22 relative to passive image guide 28. In some embodiments, sensor array 26 receives signals from emitter array 56 to provide a three-dimensional spatial position and/or a trajectory of implant 100 relative to surgical inserter 12 and/or tissue. Emitter array 56 communicates with the processor of computer 52 of navigation system 58 to generate data for display of an image on monitor 54, as described herein. In some embodiments, sensor array 26 receives signals from emitter array 56 to provide a visual representation of a position of image guide 22 relative to passive image guide 28. In some embodiments, sensor array 26 receives signals from emitter array 56 to provide a visual representation of a position of implant 100 relative to surgical inserter 12 and/or tissue. See, for example, similar surgical navigation components and their use as described in U.S. Pat. Nos. 6,021,343, 6,725,080, 6,796,988, the entire contents of each of these references being incorporated by reference herein.

Navigation system 58 is configured for acquiring and displaying medical imaging, for example, x-ray images appropriate for a given surgical procedure. In some embodiments, pre-acquired images of a patient are collected. In some embodiments, surgical navigation system 58 can include an O-Arm® imaging device 60 sold by Medtronic Navigation, Inc. having a place of business in Louisville, Colo., USA. Imaging device 60 may have a generally annular gantry housing that encloses an image capturing portion 62.

In some embodiments, navigation system 58 comprises image capturing portion 62 that may include an x-ray source or emission portion and an x-ray receiving or image receiving portion located generally or as practically possible 180 degrees from each other and mounted on a rotor (not shown) relative to a track of image capturing portion 62. Image capturing portion 62 can be operable to rotate 360 degrees during image acquisition. Image capturing portion 62 may rotate around a central point or axis, allowing image data of the patient to be acquired from multiple directions or in multiple planes. Navigation system 58 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, navigation system 58 can include C-arm fluoroscopic imaging systems, which can generate three-dimensional views of a patient. The position of image capturing portion 62 can be precisely known relative to any other portion of imaging device 60 of navigation system 58. In some embodiments, a precise knowledge of the position of image capturing portion 62 can be used in conjunction with a tracking system 64 to determine the position of image capturing portion 62 and the image data relative to the patient.

Tracking system 64 can include various portions that are associated or included with navigation system 58. In some embodiments, tracking system 64 can also include a plurality of types of tracking systems, for example, an optical tracking system that includes an optical localizer, for example, sensor array 26 and/or an EM tracking system that can include an EM localizer. Various tracking devices can be tracked with tracking system 64 and the information can be used by navigation system 58 to allow for a display of a position of an item, for example, a patient tracking device, an imaging device tracking device 66, and an instrument tracking device, for example, emitter array 56, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 68 where they may be forwarded to computer 52. Image transfer may be performed over a standard video connection or a digital link including wired and wireless. Computer 52 provides the ability to display, via monitor 54, as well as save, digitally manipulate, or print a hard copy of the received images. In some embodiments, images may also be displayed to the surgeon through a heads-up display.

In some embodiments, navigation system 58 provides for real-time tracking of the position of image guide 22 relative to passive image guide 28, implant 100 relative to surgical inserter 12 and/or tissue. Sensor array 26 is located in such a manner to provide a clear line of sight with emitter array 56, as described herein. In some embodiments, fiducial markers 70 of emitter array 56, shown in FIG. 7, communicate with sensor array 26 via infrared technology. Sensor array 26 is coupled to computer 52, which may be programmed with software modules that analyze signals transmitted by sensor array 26 to determine the position of each object in a detector space.

In some embodiments, the software program as described above includes a tools in procedure menu that is displayed on monitor 54, as shown in FIGS. 3-6, 11 and 12. The processor of computer 52 communicates with monitor 54 to indicate selected tools being implemented in the procedure. After surgical verification instrument 34 is connected with surgical inserter 12, surgical inserter 12 is selected and loaded into the tools in the procedure via the menu. In some embodiments, additional surgical instruments can be added to the tools in procedure menu. In some embodiments, an instrument can be added into the procedure via a button that prompts a user to click to add a new instrument.

Figure 5:
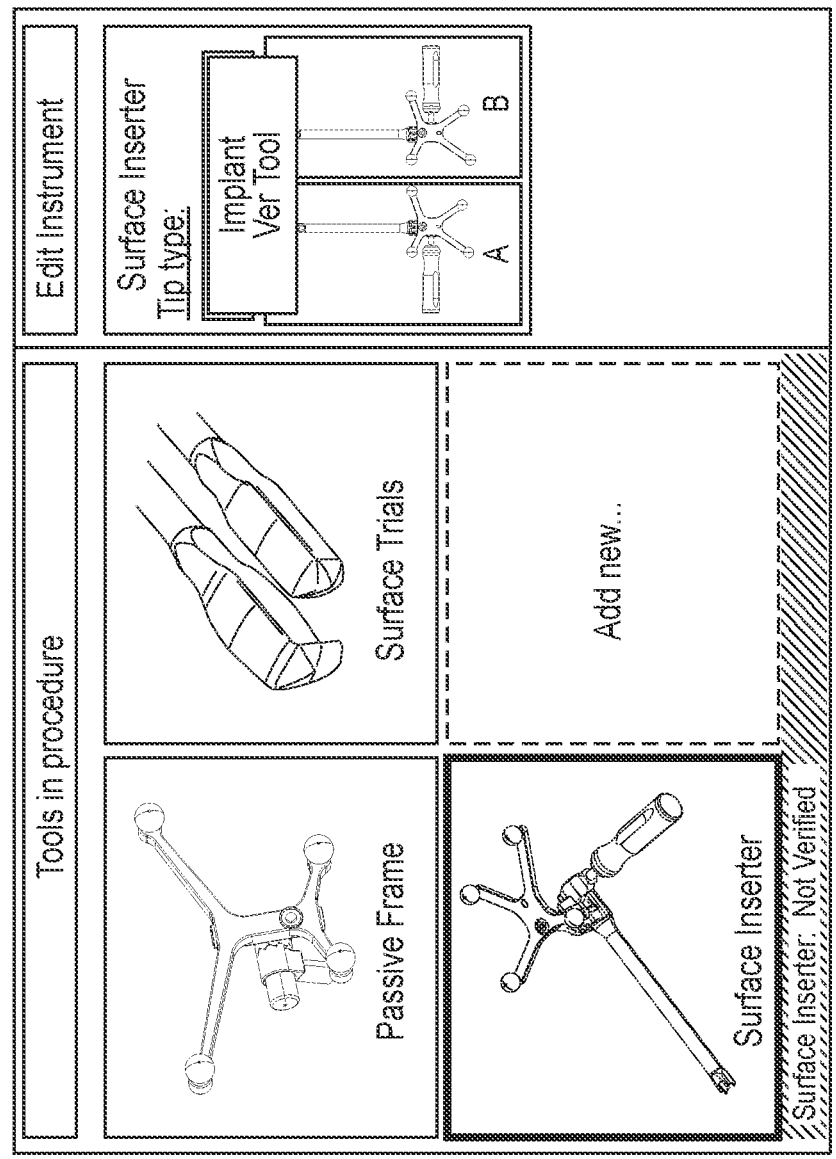
FIG. 5 is a graphical representation of a computer display of components of one embodiment of a surgical system in accordance with the principles of the present disclosure.
Figure 6:
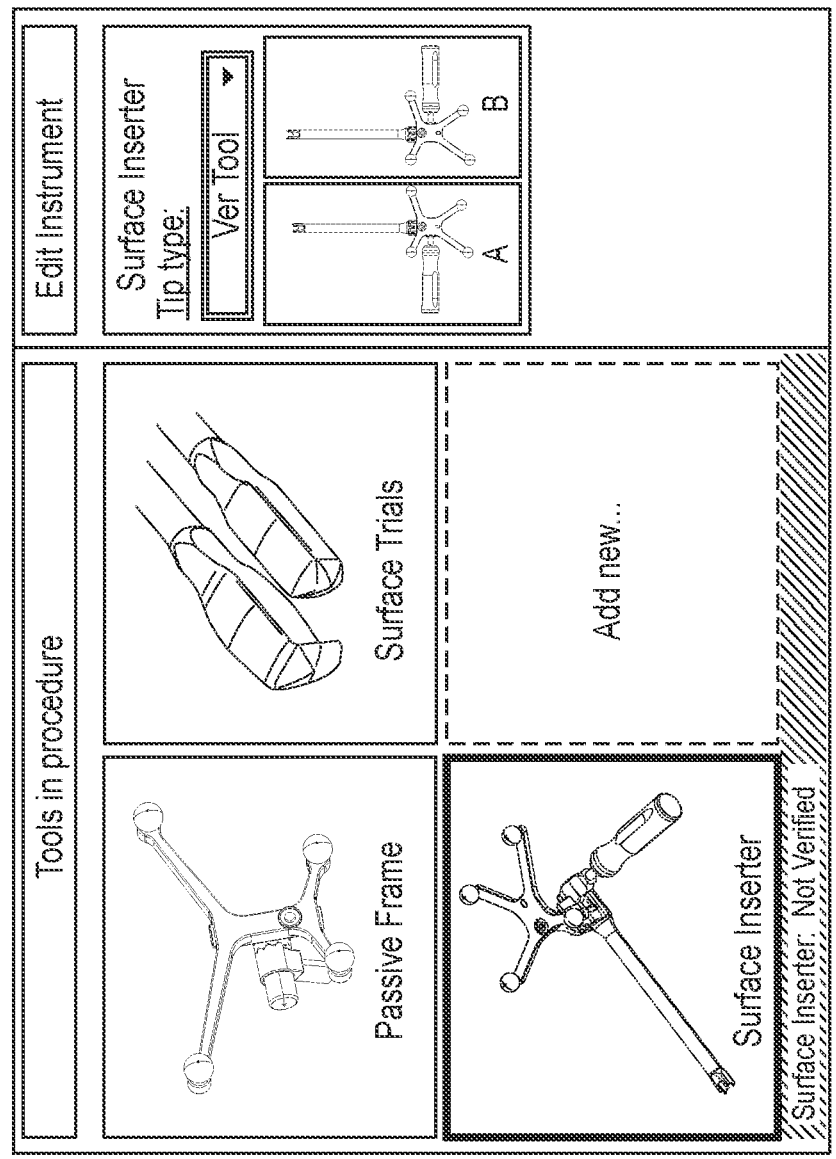
FIG. 6 is a graphical representation of a computer display of components of one embodiment of a surgical system in accordance with the principles of the present disclosure.
Figure 11:
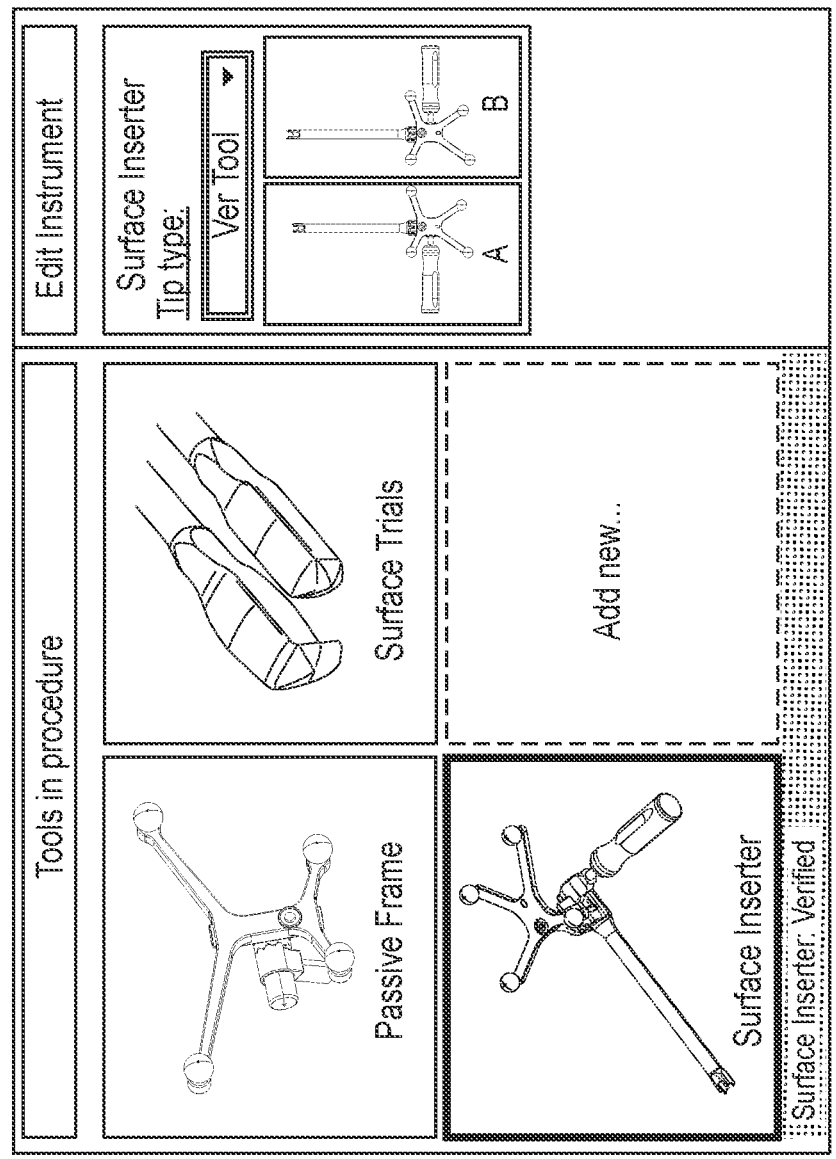
FIG. 11 is a graphical representation of a computer display of components of one embodiment of a surgical system in accordance with the principles of the present disclosure.

In some embodiments, engagement portion 20, including a tip configuration is selected, as shown in FIG. 5. In some embodiments, a pull down menu is provided to select the tip configuration. In some embodiments, surgical inserter 12 is selected and a border is disposed about the surgical inserter 12 selection and is displayed on monitor 54 to visually confirm surgical inserter 12 selection. In some embodiments, a bar is displayed on monitor 54 to visually confirm surgical inserter 12 selection. In some embodiments, the bar is a warning to a user as to whether surgical inserter 12 has been verified. In some embodiments, the bar includes diagonal hash lines, colored lines, and/or wording to indicate that surgical inserter 12 has or has not been verified, as shown in FIGS. 5, 6 and 11. In some embodiments, the bar is displayed at all times. In some embodiments, image guide 22, including image guide 22 orientation is selected and added to the tools in procedure menu, as shown in FIG. 6.

In some embodiments, surgical verification instrument 34 connected with surgical inserter 12 is positioned above passive image guide 28 and surface 36 is inserted into surface 32, as shown in FIG. 7-10. Computer 52 via the software and/or hardware verifies properly mated surfaces 32, 36 by measuring distance Y and overlapping lengths L1 and L2, and verifies that the selected surgical inserter 12 is ready for use in a surgical procedure, as shown in FIG. 11. In some embodiments, surgical inserter 12 will not be verified by computer 52 when surfaces 32, 36 are improperly mated. In some embodiments, improperly mated surfaces 32, 36 include a distance Y that is different than a distance Y that is stored as data in computer 52/software program. In some embodiments, distance Y can be different than a distance Y that is stored as data in computer 52 if either inserter 12 or surgical verification instrument 34 are bent, broken and/or damaged. In some embodiments, surgical verification instrument 34 can include dimensions that enable surgical verification instrument 34 to confirm if obstructions or bends in shaft 14 of inserter 12 are present. In some embodiments, if body 38 of surgical verification instrument 34 does not properly fit within shaft 14 of inserter 12, improper fit can indicate problems with inserter 12.

Figure 12:
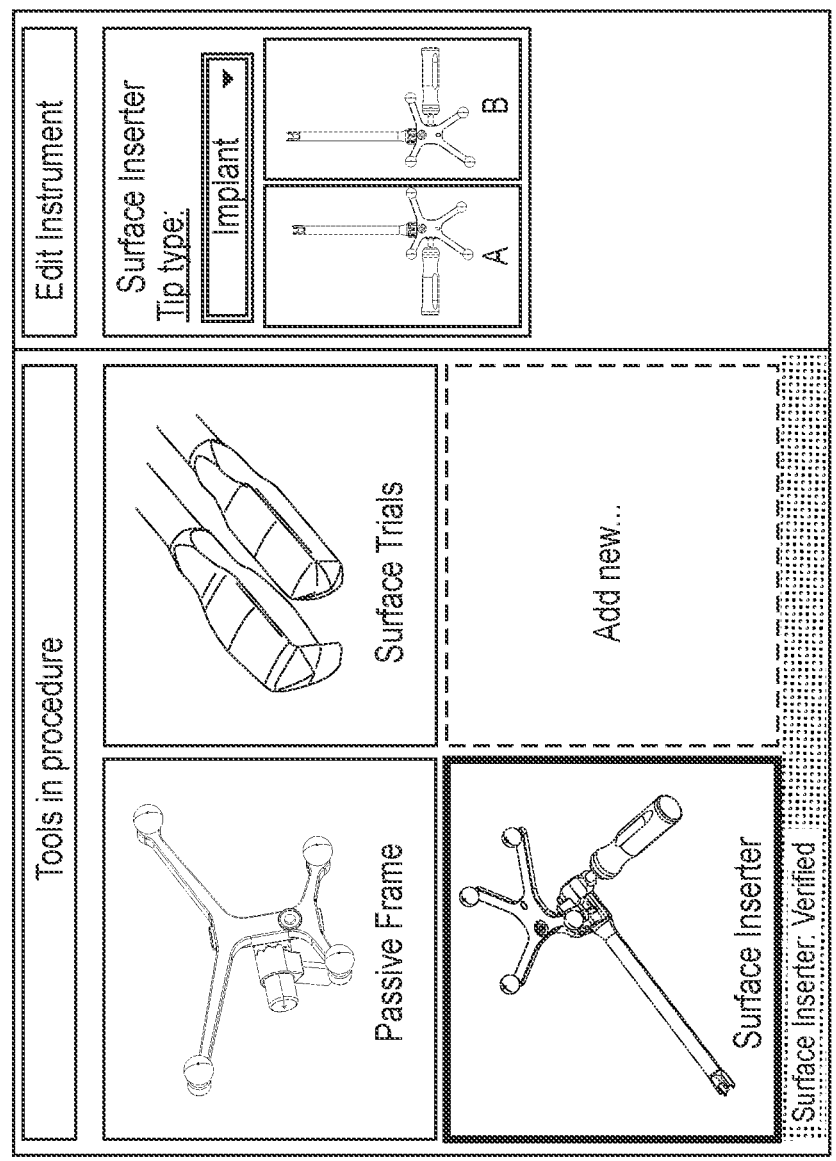
FIG. 12 is a graphical representation of a computer display of components of one embodiment of a surgical system in accordance with the principles of the present disclosure.
Figures 13, 14:
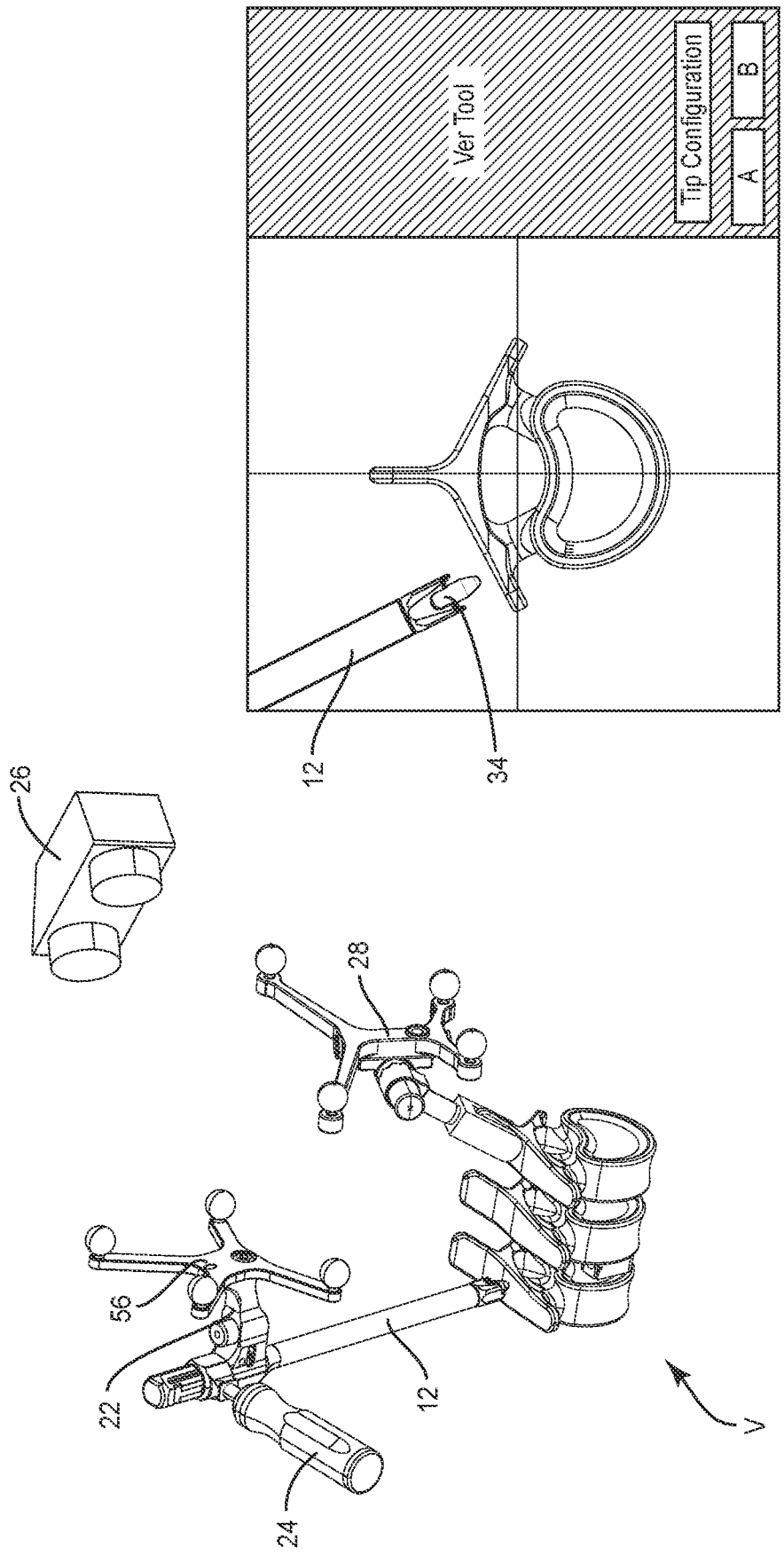
FIG. 13 is a perspective view of components of one embodiment of a surgical system in accordance with the principles of the present disclosure disposed with vertebrae.
FIG. 14 is a graphical representation of a computer display of components of one embodiment of a surgical system in accordance with the principles of the present disclosure.

In some embodiments, surgical verification instrument 34 can be selected in the tools in procedure menu and the image in the procedure displays the selected surgical verification instrument 34. In some embodiments, a drop down box is provided and displayed on monitor 54 and monitor 54 can alternate between a surgical verification instrument menu and an implant menu, as shown in FIGS. 11 and 12. In some embodiments, a drop down box is provided and is displayed on monitor 54 to enable a user to alternate between surgical verification instrument 34 and the implant menu, as shown in FIGS. 14 and 16. In some embodiments, in the tools in procedure menu, when an implant option is selected, images and right-side options in the procedure reflect implant 100 tip style, tip configuration, height and/or length. In some embodiments, implant 100 options can be provided in slider and/or drop down menus.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae V, as shown in FIGS. 7, 9, 13 and 15. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body, for example, vertebrae. In some embodiments, the components of surgical system 10 may be employed with one or a plurality of vertebra. To treat a selected section of vertebrae V, a medical practitioner obtains access to a surgical site including vertebrae in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including surgical inserter 12 and implant 100, as described herein, adjacent an area within the patient's body, for example, vertebrae. In some embodiments, a preparation instrument (not shown) can be employed to prepare tissue surfaces of vertebrae, as well as for aspiration and irrigation of a surgical region.

Figure 10:
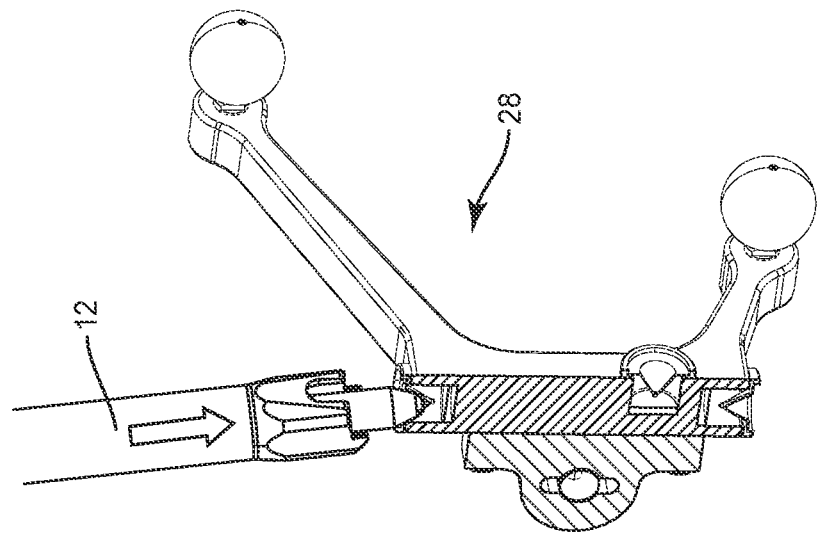
FIG. 10 is a break away view partially in cross section of components of the surgical system shown in FIG. 9.

Surgical inserter 12 is selected and image guide 22 is disposed on shaft 14. Image guide 22 is disposed relative to sensor array 26. Surgical verification instrument 34 is connected with surgical inserter 12, as shown in FIG. 2. Passive image guide 28 is fixed with vertebral tissue, for example, vertebrae V, as shown in FIG. 7. Surface 36 is engaged with surface 32 and is disposed relative to sensor array 26, as shown in FIGS. 9 and 10. The engagement between surface 32 and surface 36 in a mating configuration provides verification of the selected configuration of surgical inserter 12, as described herein. The software, as described herein, is configured to confirm that image guide 22 is disposed on surgical inserter 12 at a distance Y from passive image guide 28 to verify the selected configuration of surgical inserter 12 and to verify that the selected surgical inserter 12 is ready for use in a surgical procedure. Surgical inserter 12 is connected with implant 100, as shown in FIG. 15, for disposal in an insertion or delivery orientation, as described herein.

Surgical inserter 12 is manipulated to deliver implant 100 to the vertebral space between vertebrae. Sensor array 26 receives signals from image guide 22 to provide a three-dimensional spatial position and/or a trajectory of surgical inserter 12 and/or implant 100 relative to the vertebral space between vertebrae and/or a depth of surgical inserter 12 and/or implant 100 within the vertebral space for display on monitor 54. Surgical inserter 12 is disengageable from implant 100. In some embodiments, implant 100 provides height restoration between vertebral bodies, decompression, restoration of sagittal and/or coronal balance and/or resistance of subsidence into vertebral endplates.

In some embodiments, surgical system 10, as described herein, may include and/or be connected with various instruments including the configuration of the present disclosure, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of surgical system 10 are removed from the surgical site and the incision is closed.

Figure 18:
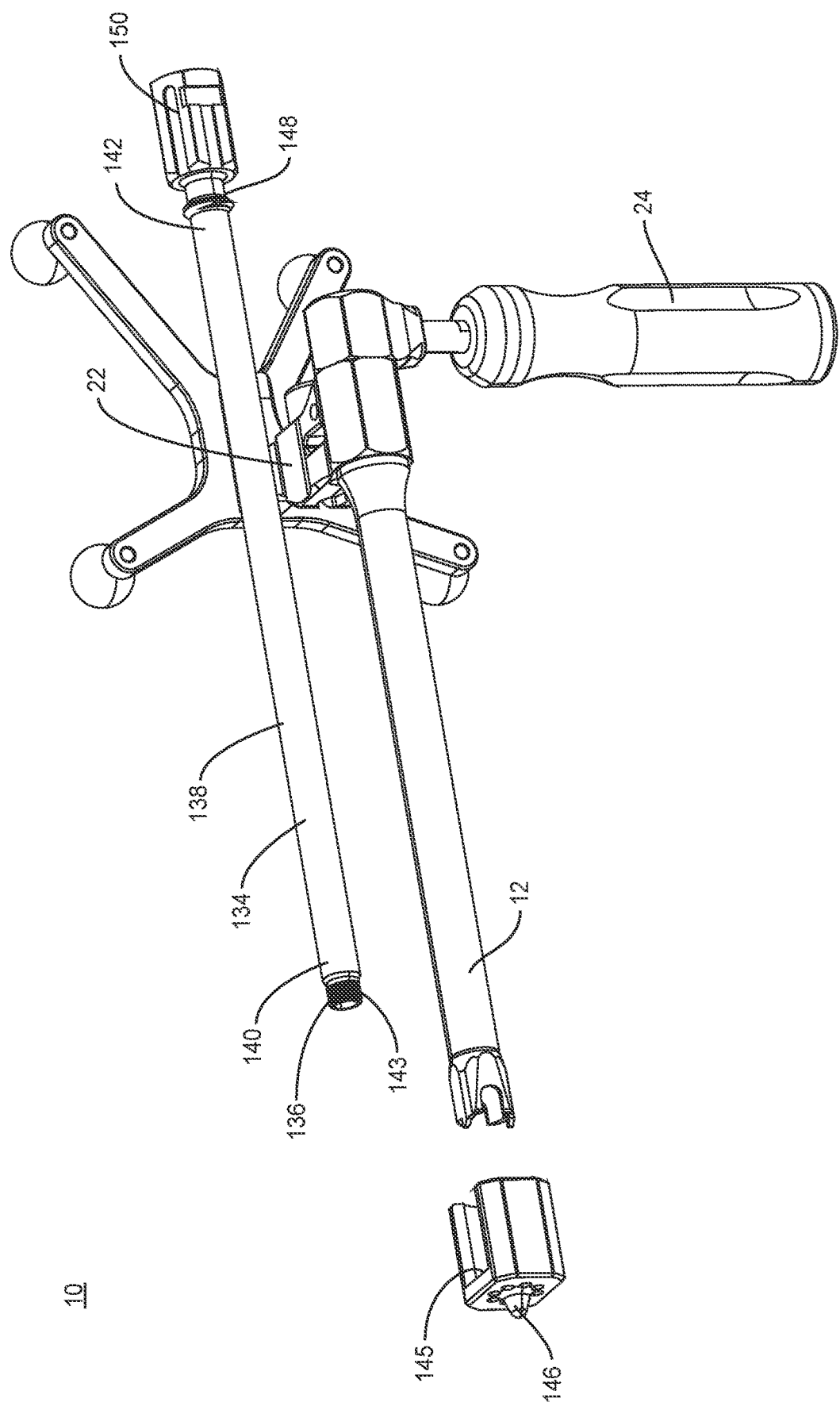
FIG. 18 is a perspective view of components of one embodiment of a surgical system in accordance with the principles of the present disclosure.
Figure 19:
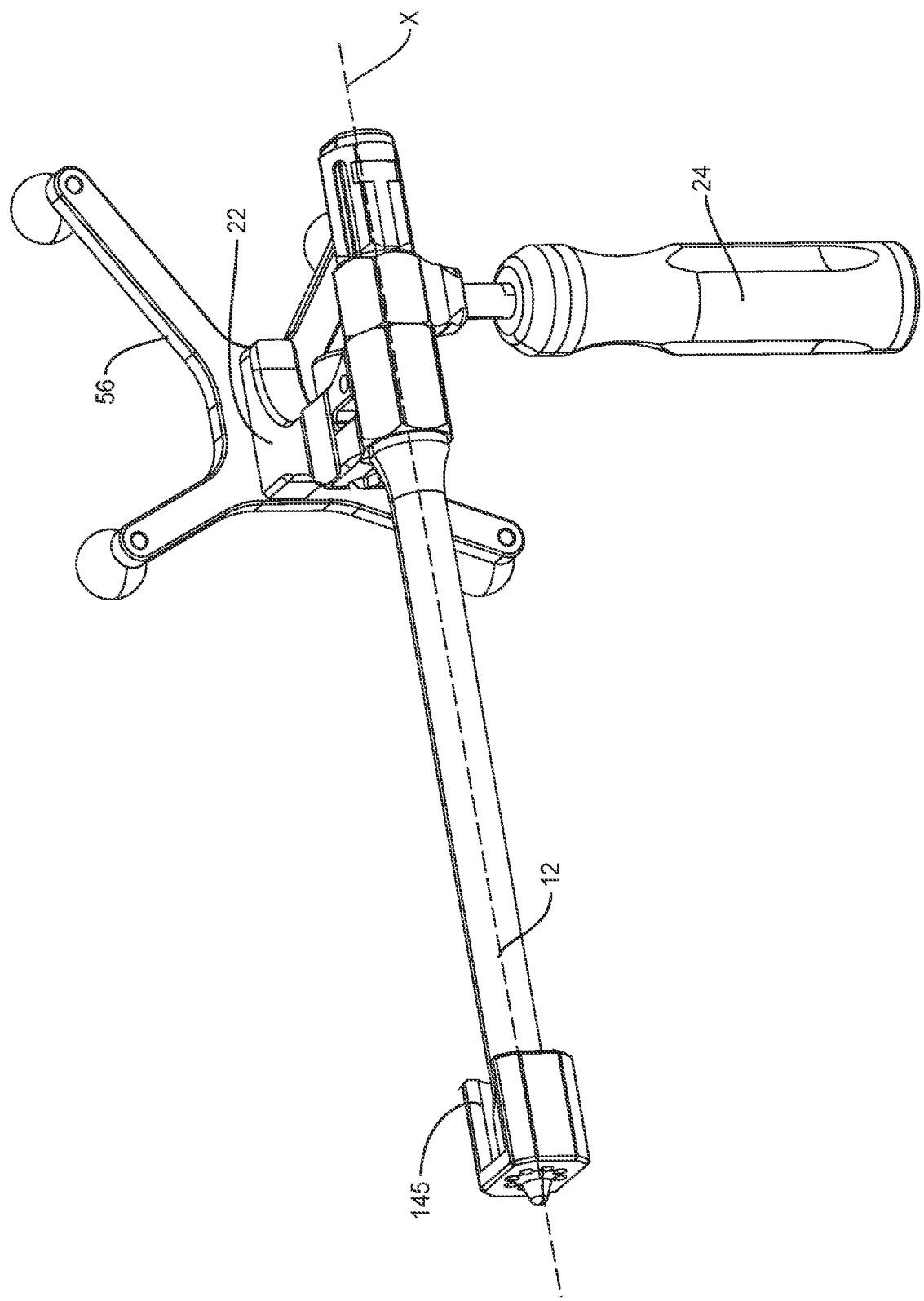
FIG. 19 is a perspective view of the components shown in FIG. 18.

In some embodiments, as shown in FIGS. 18-21, surgical system 10 includes a surgical verification instrument 134, similar to surgical verification instrument 34, described herein, configured for connection with surgical inserter 12, as shown in FIG. 18. Surgical verification instrument 134 includes a body 138 that extends between an end 140, an end 142 and is disposed along longitudinal axis X, as shown in FIG. 19. Surgical verification instrument 134 is configured for coaxial connection with surgical inserter 12 via disposal of surgical verification instrument 134 through cavity 44 of surgical inserter 12. End 140 includes a surface 136 that defines a threaded portion 143 configured for threaded connection with an internally threaded cap 145. Threaded cap 145 is configured for connection with engagement portion 20 of surgical inserter 12, as shown in FIG. 19.

Figure 21:
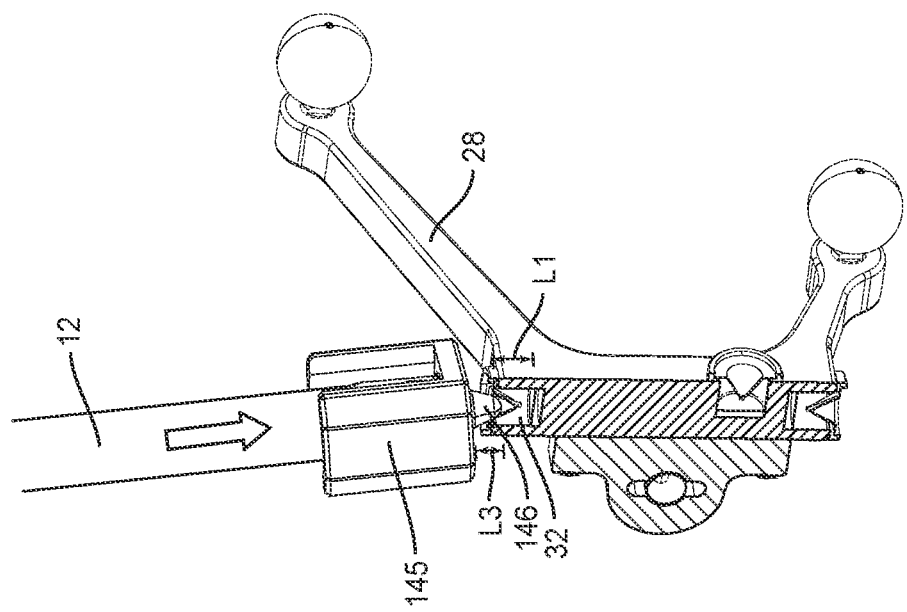
FIG. 21 is a break away view partially in cross section of the components the surgical system shown in FIG. 20.
Figure 20:
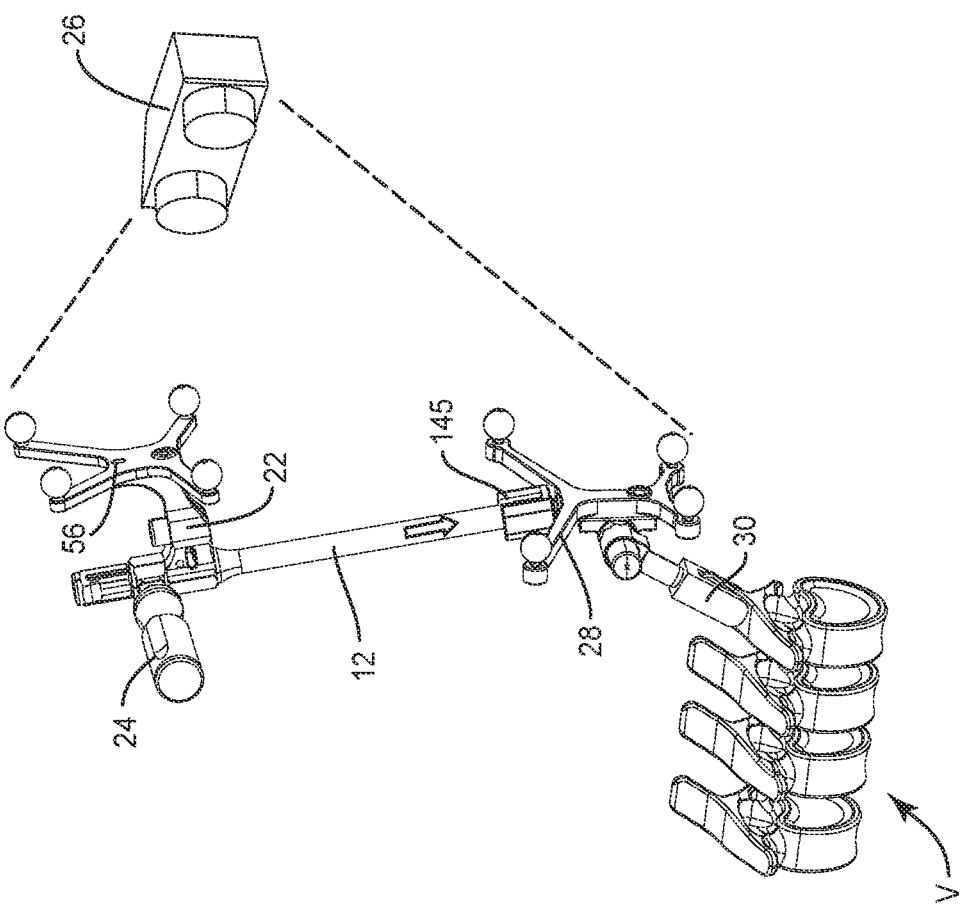
FIG. 20 is a perspective view of components of one embodiment of a surgical system in accordance with the principles of the present disclosure disposed with vertebrae.

Threaded cap 145 includes a surface 146, similar to surface 36 of surgical verification instrument 34, which is engageable with surface 32 of passive image guide 28 in a mating configuration. Surface 146 includes a cone tipped configuration that is engaged in a mating configuration with a correspondingly configured recess 33 of surface 32. Surface 146 includes a length L3, as shown in FIG. 21. Length L3 corresponds to length L1 of recess 33 and an equal length to L3. In some embodiments, Length L3 is in a range from 1 to about 20 mm. In some embodiments, surface 146 may be variously configured including tapered, cone shaped, threaded and/or ball shaped. In some embodiments, surface 146 may include alternate cross section configurations, for example, triangular, scalene triangle, right triangle, pyramidal, square, circular, oval, rectangular, pentagonal, hexagonal, heptagonal, octagonal, nonagon, parallelogram, rhombus, U-shaped, V-shaped, W-shaped, concave, crescent, heart, cross, arrow, cube, cylinder, star, a wavy line, semicircular, ring, quatrefoil, irregular, uniform, non-uniform, tapered or a combination thereof. In some embodiments, surface 146 may include alternate surface configurations, for example, rough, arcuate, undulating, mesh, porous, semi-porous, dimpled and/or textured.

End 142 includes an outer surface that defines a threaded portion 148, as shown in FIG. 18. Threaded portion 148 is configured for threaded engagement with threaded portion 48 of cavity 42 of surgical inserter 12. Threaded portion 148 engages with threaded portion 48 of cavity 44 when surgical verification instrument 134 is disposed within cavity 44 of surgical inserter 12 to connect surgical verification instrument 134 with surgical inserter 12. End 142 includes a handle 150.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
   a first surgical instrument having a selected configuration and an image guide disposed relative to a sensor to communicate a signal representative of a position of the image guide, the first surgical instrument extends between a first end and a second end and defines a longitudinal axis;
   a passive image guide fixable with vertebral tissue and disposed relative to the sensor to communicate a signal representative of a position of the passive image guide, the passive image guide including a first surface; and a second surgical instrument being coaxially connected with the first surgical instrument, the second surgical instrument extending between a first end and a second end including a second surface having a projection, the first end of the second surgical instrument being fixed with the first end of the first surgical instrument such that the projection extends from the second end of the first surgical instrument and is engaged with the first surface in a mating configuration to provide verification of the selected configuration.

2. A surgical system as recited in claim 1, wherein the mating configuration includes the image guide of the first surgical instrument being disposed a selected distance from the passive image guide.

3. A surgical system as recited in claim 1, wherein the passive image guide includes a frame fixable with the vertebral tissue and the mating configuration includes the image guide of the first surgical instrument being disposed a selected distance from the frame.

4. A surgical system as recited in claim 1, wherein the first surgical instrument is selected from a plurality of surgical inserters.

5. A surgical system as recited in claim 1, wherein the first surgical instrument is selected from at least a first surgical inserter having a first selected configuration and a second surgical inserter having a second selected configuration.

6. A surgical system as recited in claim 1, wherein the verification includes indicia of the selected configuration.

7. A surgical system as recited in claim 1, wherein the sensor communicates with a processor to confirm the mating configuration and provide verification of the selected configuration.

8. A surgical system as recited in claim 7, wherein the processor provides verification via audible, tactile or visual indicia.

9. A surgical system as recited in claim 7, wherein the processor communicates with a display monitor to provide verification via the display monitor.

10. A surgical system as recited in claim 1, wherein the projection is a tapered projection matingly engaged with a correspondingly configured recess of the first surface.

11. A surgical system as recited in claim 1, wherein the projection is a cone shaped projection matingly engaged with a correspondingly configured cone shaped recess of the first surface.

12. A surgical system as recited in claim 1, wherein the projection is a ball shaped projection matingly engaged with a socket shaped recess of the first surface.

13. A surgical system as recited in claim 1, wherein the second surgical instrument includes an internally threaded cap connectable with a threaded portion of the second surface.

14. A surgical system as recited in claim 1, wherein the first ends are threadably engaged to fix the first end of the second surgical instrument with the first end of the first surgical instrument.

15. A surgical instrument comprising:

a body extending between a first end and a second end including a first surface having a projection, the body being coaxially connectable with a surgical inserter extending between a first end and a second end and defining a longitudinal axis, the surgical inserter having a selected configuration and an image guide disposed relative to a sensor to communicate a signal representative of a position of the image guide, the first end of the body being fixed with the first end of the surgical inserter such that the projection extends from the second end of the surgical inserter and engages a second surface of a passive image guide fixable with vertebral tissue and disposed relative to the sensor to communicate a signal representative of a position of the passive image guide, the projection being engageable with the second surface in a mating configuration to provide verification of the selected configuration.

16. A surgical instrument as recited in claim 15, wherein the mating configuration includes the image guide of the first surgical instrument being disposed a selected distance from the passive image guide.

17. A surgical instrument as recited in claim 15, wherein the passive image guide includes a frame fixable with the vertebral tissue and the mating configuration includes the image guide of the first surgical instrument being disposed a selected distance from the frame.

18. A surgical instrument as recited in claim 15, wherein the sensor communicates with a processor to confirm the mating configuration and provide verification of the selected configuration.

19. A surgical instrument as recited in claim 15, wherein the mating configuration includes the first surface having a tapered projection matingly engaged with a correspondingly configured recess of the second surface.

20. A method for treating a spine, the method comprising the steps of:

selecting a first surgical instrument having a selected configuration and an image guide disposed relative to a sensor, the sensor communicating a signal representative of a position of the image guide, the first surgical instrument extends between a first end and a second end and defining a longitudinal axis;

coaxially connecting a second surgical instrument with the first surgical instrument, the second surgical instrument extending between a first end and a second end including a projection;

fixing the first end of first surgical instrument with the first end of the second surgical instrument; and engaging the projection with a passive image guide fixed with vertebral tissue and disposed relative to the sensor to communicate a signal representative of a position of the passive image guide, the projection being engageable with the passive image guide in a mating configuration to provide verification of the selected configuration.

* * * * *